United States Patent [19]

Taylor

[11] 4,248,235
[45] Feb. 3, 1981

[54] VALVE ASSEMBLIES

[75] Inventor: Joseph P. Taylor, Hythe, England

[73] Assignee: Smiths Industries Limited, London, England

[21] Appl. No.: 922,249

[22] Filed: Jul. 5, 1978

[30] Foreign Application Priority Data

Jul. 14, 1977 [GB] United Kingdom ............... 29712/77

[51] Int. Cl.³ ............................................. A61M 25/00
[52] U.S. Cl. ................................... 128/349 R; 137/223
[58] Field of Search ..................... 128/349 R, 349 BV; 137/223

[56] References Cited

U.S. PATENT DOCUMENTS

| 2,233,096 | 2/1941 | Goldsmith | 137/223 |
| 3,477,438 | 11/1969 | Allen et al. | 128/349 BV |
| 3,565,078 | 2/1971 | Vailliancourt | 137/223 X |

Primary Examiner—Harry N. Haroian
Attorney, Agent, or Firm—Pollock, Vande Sande & Priddy

[57] ABSTRACT

A valve assembly comprises a resilient housing of plastic material and a valve element in the form of a unitary plastic body located within the housing. The body is closed at one end by a dish-shape portion having a circumferential lip which forms a seal with the housing. The body has a tongue formed in its wall, one end of the tongue being provided with an inwardly directed tooth. By inserting a tube or rod within the valve element to engage the tooth, the tongue can be displaced outwardly and the overlying part of the housing can thereby be distorted away from the lip to permit fluid flow through the housing. The valve assembly may be used to seal one end of the inflation line of a cuffed medico-surgical tube.

7 Claims, 6 Drawing Figures

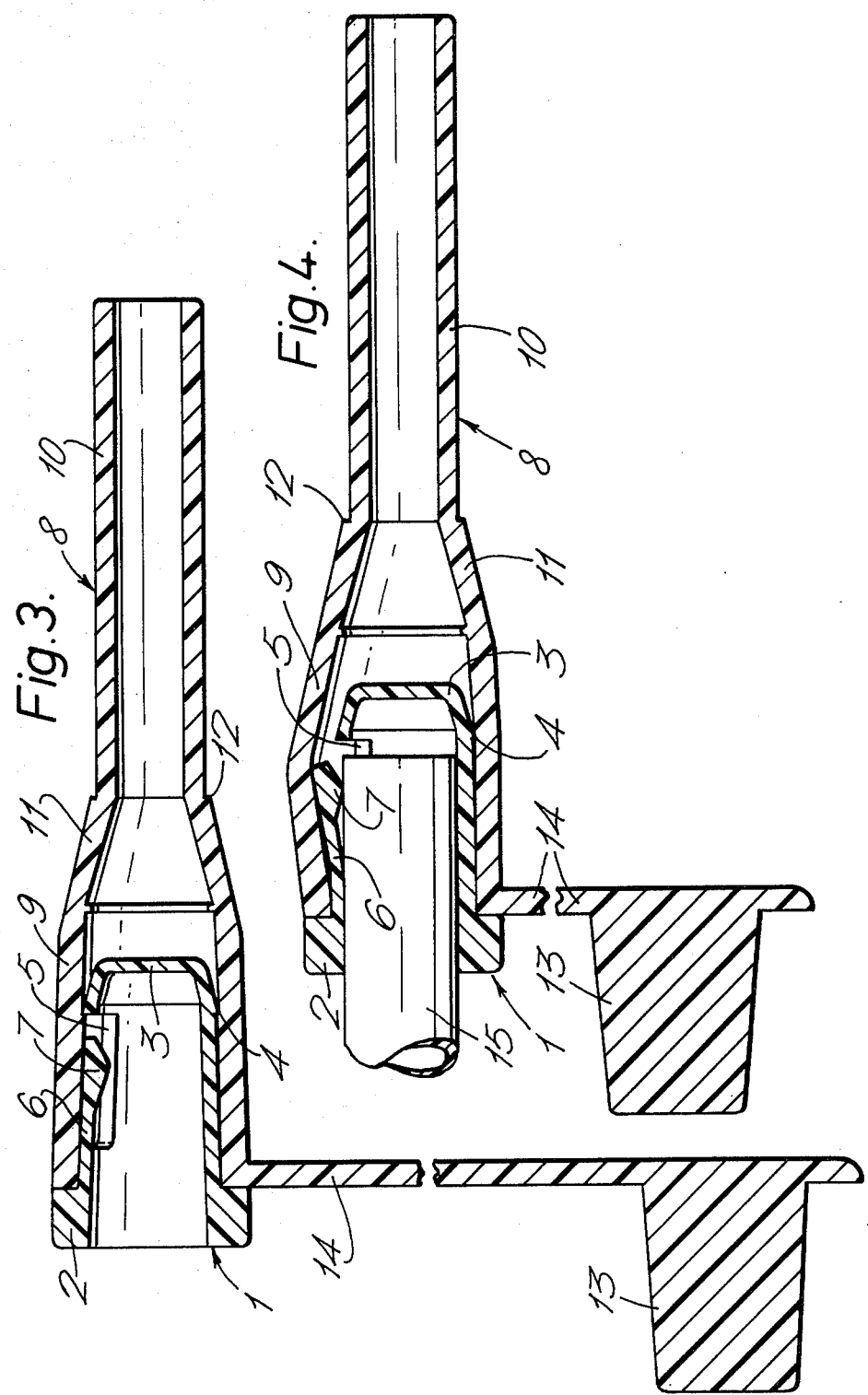

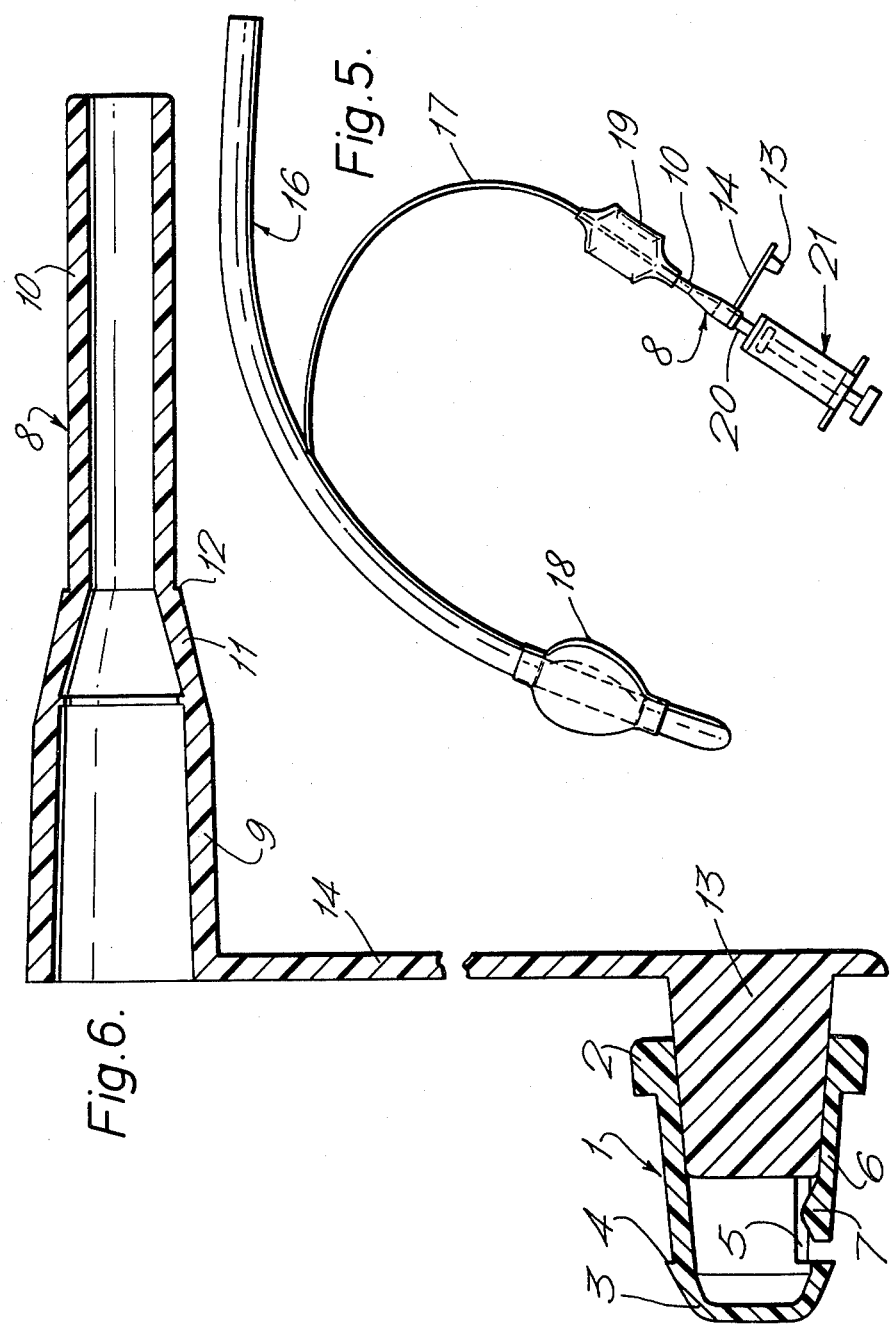

VALVE ASSEMBLIES

BACKGROUND OF THE INVENTION

This invention relates to valve assemblies, valve elements for use in such assemblies, and medico-surgical tubes including such assemblies.

The invention is particularly, though not exclusively concerned with valve elements and valve assemblies for use in medico-surgical tubes of the kind provided with an inflatable cuff around a portion of the tube. In such an application, the valve assembly may be provided at one end of a fluid line making connection with the interior of the cuff.

Valve assemblies for use in such medico-surgical tubes are known in which the assembly includes a resilient housing having a passageway therethrough which is normally blocked by a plug located in the passageway. This known form of valve assembly can be opened by inserting within the passageway the tip of a syringe which engages with projections formed on the inside of the housing and thereby distorts the housing away from the plug to form a gas passageway between the plug and the housing.

While this known form of valve assembly has proved useful on medico-surgical tubes, some users of such tubes prefer not to use valves but instead to close the fluid line to the cuffs by means of a stopper or similar device. It has therefore, until now, been necessary either to manufacture two ranges of medico-surgical tubes, one with valves and one without valves, or to rely on the user himself making somewhat difficult and unreliable adaptations of a tube provided with a valve, according to his preferred method of use.

BRIEF SUMMARY OF THE INVENTION

It is an object of the present invention to provide a valve assembly, a valve element for such an assembly and a medico-surgical tube including such as assembly that can be manufactured cheaply and that can be used to alleviate the above disadvantage.

According to one aspect of the present invention there is provided a valve assembly including a resilient housing, a unitary body located within said housing, said body being adapted for sealing engagement within said housing so as thereby to prevent fluid flow through said housing, wherein said body is adapted for engagement by an actuating member inserted within it, such as thereby to have a part at least of the body displaced outwardly by said actuating member and to distort said housing away from said body such as to permit fluid flow through said housing.

According to another aspect of the present invention there is provided a valve element comprising a unitary body having a portion for sealing engagement within a resilient housing, so as to prevent fluid flow through the housing, wherein said body is adapted for engagement by an actuating member inserted within it, such as thereby to have a part at least of the body displaced outwardly by said actuating member to distort said housing away from said sealing portion of the body such as to permit fluid flow through said housing.

The body may have an inwardly-directed surface formation adapted for engagement by said actuating member. The surface formation may be formed at one end of an elongate portion formed in the wall of said body.

The body of a valve assembly according to the present invention may be readily inserted and removed from the housing by the user thereby enabling a valve assembly including such a body to be easily modified.

According to a further aspect of the present invention there is provided a medico-surgical tube having a cuff encompassing a portion of the tube length and a fluid passageway which connects with the interior of said cuff and which is provided at one end with a valve assembly for preventing fluid escape from said cuff, wherein said valve assembly includes a resilient housing, a unitary body located within said housing, said body being adapted for sealing engagement with said housing so as thereby to prevent fluid flow through said passageway, and wherein said body is adapted for engagement by an actuating element inserted within it, such as thereby to have a part at least of the body displaced outwardly by said actuating element and to distort said housing away from the body such as to permit fluid flow through said housing.

A valve assembly, a valve element for such an assembly, and a medico-surgical tube including such a valve assembly each in accordance with the present invention, will now be described, by way of example, with reference to the accompanying drawings.

BRIEF DESCRIPTION OF THE DRAWINGS

FIGS. 3 and 4 are sectional elevations of a valve assembly including the valve element shown in FIGS. 1 and 2 and in a closed and open condition respectively;

FIG. 5 illustrates the valve assembly in use on a medico-surgical tube; and

FIG. 6 illustrates an alternative arrangement of valve assembly.

Figure 1:
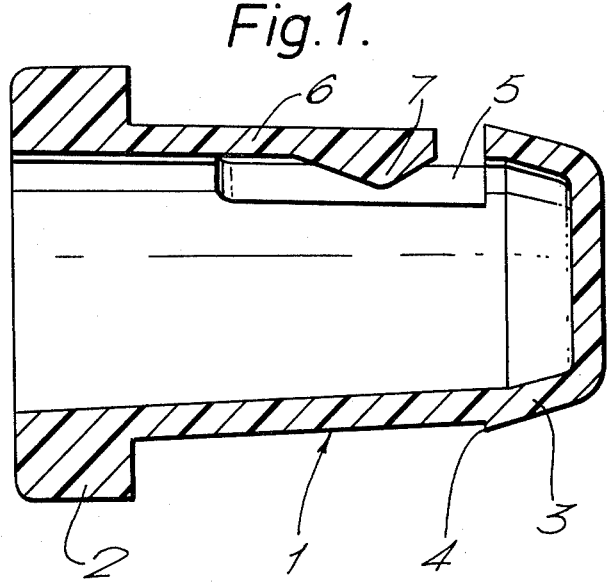
FIG. 1 is a sectional elevation of a valve element.
Figure 2:
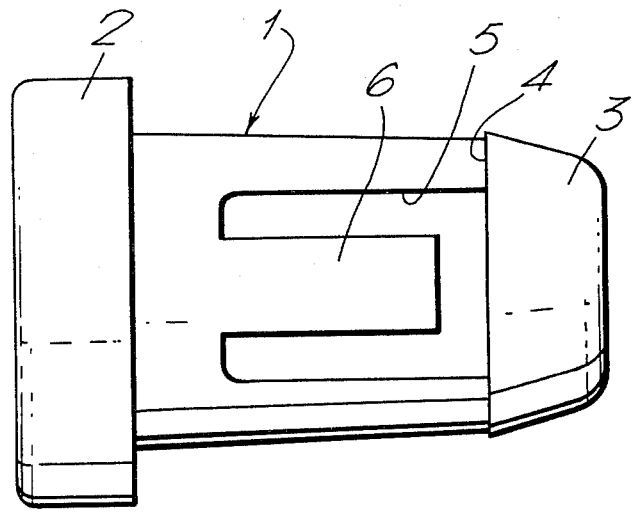
FIG. 2 is a plan view of the valve element shown in FIG. 1.

The valve element, as shown in FIGS. 1 and 2, is a unitary moulded body 1 of acetal plastic and is of a generally cylindrical shape, being hollow and open at one end. The body 1 has a radially extending flange 2 at its open end and tapers slightly to a reduced diameter at its forward end where it is closed by a dished portion 3. A circumferential edge of the dished portion 3 projects outwardly of the surface of the body 1 thereby forming a lip 4. Rearwardly of the lip 4, a 'U'-shaped cut-away portion 5 is formed in the wall of the body 1 to define a tongue 6 that extends along a part of the length of the body. The tongue 6 has at its tip, a tooth 7 that projects into the interior of the body 1.

With reference to FIG. 3, the valve assembly has a tubular polyvinyl chloride valve housing 8 formed with a rear portion 9 into which the body 1 is inserted with its flange 2 abutting the end of the housing. The housing 8 also has a forward portion 10 which is of a smaller diameter and which connects with the rear portion 9 via an intermediate tapering portion 11. A small rim 12 is formed around the circumference of the outer surface of the housing 8, between the forward portion 10 and the tapering portion 11. The housing 8 is also provided with a stopper 13 formed at the end of a flexible tag 14 that is integral with the housing and extends outwardly of it at its rear end. The stopper 13 may be used to close the housing 8 when the valve body 1 is not in place, by bending the tag 14 and inserting the stopper in the rear end of the housing. When the valve body 1 is in place, it forms a tight fit with the rear portion 9 of the housing 8, the housing being sufficiently resilient to ensure a fluid-tight seal about the lip 4 of the dished portion 3.

The valve assembly may be 'opened', to allow passage of fluid along the housing 8, by distorting the housing away from the dished portion 3 of the body 1. This is done by inserting an actuating tube 15 in the rear end of the valve body 1 and pushing it forwards of the valve body as shown in FIG. 4. The tube 15 has an external diameter that is approximately the same as the internal diameter of the valve body 1 so that, as the tube is pushed forwards, it engages with the tooth 7 thereby causing the tongue 6 and the overlying portion of the housing 8 to be displaced outwardly. A passageway is thus formed between the housing 8 and the dished portion 3 to permit the flow of gas or liquid through the cut-away portion 5. When the tube 15 is withdrawn, the resilience of the housing 8 urges it firmly into contact with the lip 4 of the dished portion 3 to re-seal and 'close' the valve assembly. The lip 4 also ensures that the valve element is not inadvertently pulled out of the housing 8 upon withdrawal of the tube 15.

With reference to FIG. 5 the valve assembly is illustrated in use with a cuffed endotracheal tube 16. The forward portion 10 of the valve assembly housing 8 is connected to the end of an air-line 17 which makes connection with the interior of a cuff 18 secured around a portion of the endotracheal tube 16 at one end. A pilot balloon 19 embraces the forward end 10 of the housing 8 and a short portion of the air-line 17, the interior of the pilot balloon 19 being in communication with the air-line 17 so as to be inflated or deflated in accordance with inflation or deflation of the cuff 18 and hence give an indication of its condition. The cuff 18 is inflated by inserting the nose 20 of a syringe 21 within the valve assembly to distort the housing 8 in the manner described above. By depressing the plunger of the syringe 20 a measured quantity of air or other fluid can be delivered to the cuff 18 to inflate it to the required extent; upon removal of the syringe an air-tight seal is formed, preventing deflation of the cuff. When it is required to deflate the cuff 18, the syringe 20, or any other suitably shaped member, can be inserted within the valve body 1 to distort the housing 8 away from dished-portion 3 and thereby allow the retained air to escape.

One advantage of the form of valve element described is that it may readily be inserted in or removed from the housing 8. For this reason, the valve housing 8 and body 1 may be supplied to the user in the manner shown in FIG. 6, in which the body 1 is attached to the housing by means of the tag 14 and stopper 13 which is inserted in the open end of the body. Thus, the valve body 1 can be pushed into position within the end of the housing 8 using the stopper 13 and tag 14 to aid insertion, the stopper subsequently being pulled out of the body. If preferred, however, the user of such an assembly could discard the valve body 1 by removing it from the stopper 13 prior to use.

When such a valve assembly is attached to the end of the air-line of a cuffed endotracheal tube the user of the tube is able either to use the valve assembly in conjunction with the valve body 1, or to effect sealing of the air-line 17 by, for example, pinching it closed and inserting the stopper 13 in the end of the housing. It is not therefore necessary to manufacture two different endotracheal tubes, one with a valve and one without, since the same tube can be adapted easily by the user according to his preferred method of inflating the cuff.

It is envisaged that the valve element could be made of material other than an acetal plastic, such as, for example, nylon, ABS, polycarbonates, stainless-steel or silver. The valve housing 8 could likewise be made of any suitable resilient material.

Although the valve element described has but a single tongue 6 and tooth 7, it may be found preferable in some cases to have more than one tongue. Other forms of valve element, in addition to the tongue and tooth configuration, are also envisaged, for example, instead of having a member projecting from the wall of the valve body into its interior, the interior could be tapered to a greater extent than is shown in the accompanying drawings. It would, in this case, be necessary to use an actuating tube, the diameter of which would be sufficiently large, when inserted, to distort the wall of the valve body outwardly and cause a gas passage to be formed between the housing and the valve element.

The valve element and the valve assembly are not restricted to use with endotracheal tubes but may be used, for example, in pneumatic tyres or other articles such as footballs, inflatable life-saving jackets, air-mattresses and -pillows.

I claim:

1. A valve assembly comprising a resilient housing and a unitary body located within said housing, said body being of generally tubular shape and having one end open and the other end closed by a generally dish-shaped sealing portion, said sealing portion having a circumferencial lip for engagement with said housing so as thereby to prevent fluid flow through said housing, a through aperture in said body, and means resiliently supported on said body and extending over said aperture, said means including a part which extends inwardly into the interior of said tubular body to thereby be adapted for movement outwardly by an actuating member inserted into said one open end of said body, whereby outward movement of said portion causes outward distortion of said housing away from said lip to thereby permit flow through said housing between said lip and said aperture and via said aperture into the interior of said tubular body.

2. A valve assembly according to claim 1 wherein said body includes an elongate portion, said elongate portion being mounted at one end with said body, and wherein said inwardly-directed surface formation is provided at the other end of said elongate portion so that the said elongate portion is displaced outwardly at its other end by said actuating member upon engagement with said inwardly-directed surface formation.

3. A valve assembly according to claim 1 or claim 2 wherein said body is of plastic material.

4. A valve assembly according to claim 1 or claim 2 wherein said housing is of resilient plastic material.

5. A medico-surgical tube of the kind comprising a tube; a cuff, said cuff encompassing a portion of said tube length; a fluid passageway, said fluid passageway connecting with the interior of said cuff; and a valve assembly, said valve assembly being provided at one end of said fluid passageway for preventing fluid escape from said cuff, wherein said valve assembly comprises a resilient housing coupled with said fluid passageway, and a unitary body located within said housing, said body being of generally tubular shape and having one end open and the other end closed by a generally dish-shaped sealing portion, said sealing portion having a circumferential lip for engagement with said housing so as thereby to prevent fluid flow through said housing and hence along said fluid passageway, a through aperture in said body, and means resiliently supported on said body and extending over said aperture, said means including a part which extends inwardly into the interior of said tubular body to thereby be adapted for movement outwardly by an actuating member inserted into said one open end of said body, whereby outward movement of said portion causes outward distortion of said housing away from said lip to thereby permit flow through said housing between said lip and said aperture and via said aperture into the interior of said tubular body.

6. A valve assembly comprising a resilient housing and a unitary body located within said housing, said body being of generally tubular shape and having one end open and the other end closed by a generally dish-shaped sealing portion, said sealing portion having a circumferential lip for engagement with said housing, wherein said body has a 'U'-shape aperture in its wall, said 'U'-shape aperture defining an elongate portion mounted at one end with said body, wherein said elongate portion is provided at its other end with an inwardly-directed surface formation, said surface formation being arranged so that insertion of an actuating member within said body engages said surface formation and thereby displaces said other end of said elongate portion outwardly and hence distorts a part of said housing away from said lip to permit fluid flow through said housing via said aperture.

7. A medico-surgical tube of the kind comprising a tube; a cuff, said cuff encompassing a portion of said tube length; a fluid passageway, said fluid passageway connecting with the interior of said cuff; and a valve assembly according to claim 2 or claim 6, said valve assembly being provided at one end of said fluid passageway for preventing fluid escape from said cuff.

* * * * *